(12) United States Patent
Dakin et al.

(10) Patent No.: US 11,564,627 B2
(45) Date of Patent: Jan. 31, 2023

(54) FORCE SENSING CATHETER SYSTEM

(71) Applicant: St. Jude Medical International Holding S.à r.l., Luxembourg (LU)

(72) Inventors: Gregory Dakin, Edina, MN (US); Quinn Butler, Coon Rapids, MN (US); Xiangyang Zhang, Maple Grove, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 972 days.

(21) Appl. No.: 16/375,558

(22) Filed: Apr. 4, 2019

(65) Prior Publication Data

US 2019/0307505 A1    Oct. 10, 2019

Related U.S. Application Data

(60) Provisional application No. 62/653,210, filed on Apr. 5, 2018.

(51) Int. Cl.
*A61B 5/00* (2006.01)
*A61B 18/14* (2006.01)
*A61B 90/00* (2016.01)
*A61B 18/00* (2006.01)
*G01L 1/24* (2006.01)

(52) U.S. Cl.
CPC .......... *A61B 5/6852* (2013.01); *A61B 5/6885* (2013.01); *A61B 18/1492* (2013.01); *A61B 90/06* (2016.02); *A61B 2018/00011* (2013.01); *A61B 2018/00351* (2013.01); *A61B 2018/00577* (2013.01); *A61B 2090/064* (2016.02); *A61B 2090/065* (2016.02); *A61B 2562/0266* (2013.01); *G01L 1/242* (2013.01)

(58) Field of Classification Search
CPC . A61B 5/6852; A61B 5/6885; A61B 18/1492; A61B 90/06; A61B 2018/00011; A61B 2018/00351; A61B 2018/00577; A61B 2090/064; A61B 2090/065; A61B 2562/0266; G01L 1/242
See application file for complete search history.

(56) References Cited

U.S. PATENT DOCUMENTS

| 8,567,265 | B2 | 10/2013 | Aeby et al. |
| 8,649,847 | B1 * | 2/2014 | Park ................... A61B 10/0233 604/95.05 |
| 2017/0319269 | A1 | 11/2017 | Oliverius et al. |
| 2019/0038228 | A1 | 2/2019 | Daly et al. |

FOREIGN PATENT DOCUMENTS

| WO | 2012142588 A1 | 10/2012 |
| WO | 2018142372 A1 | 8/2018 |

* cited by examiner

*Primary Examiner* — Jung Kim
(74) *Attorney, Agent, or Firm* — Armstrong Teasdale LLP

(57) ABSTRACT

Aspects of the present disclosure are directed toward systems and methods for detecting force applied to a distal tip of a medical catheter. A medical catheter includes a deformable body near a distal tip of the catheter that deforms in response to a force applied at the distal tip, and a sensor detects various components of the deflection. Processor circuitry may then, based on the detected components of the deformation, determine a force applied to the distal tip of the catheter.

20 Claims, 12 Drawing Sheets

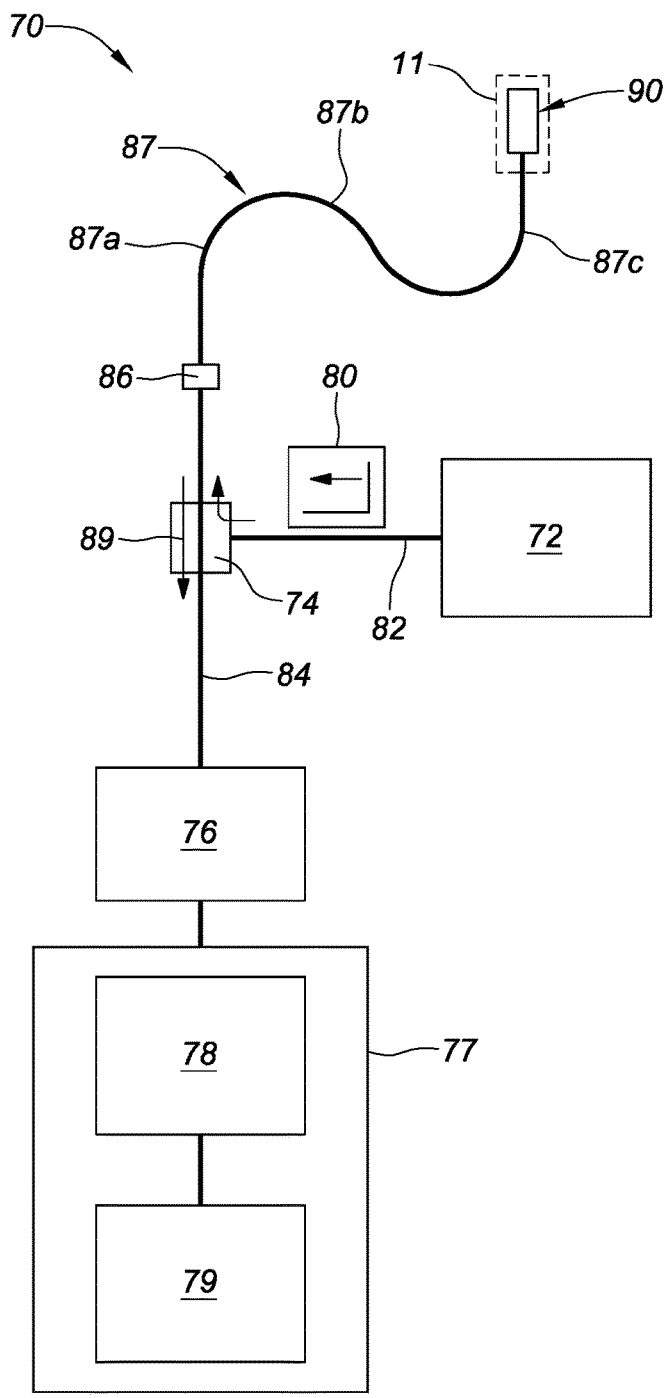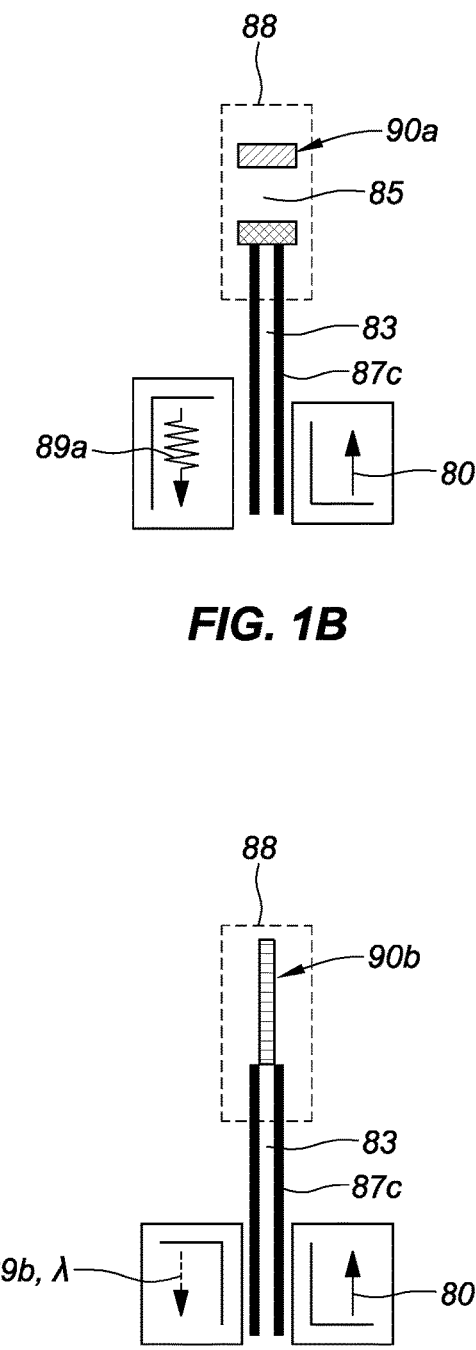
FIG. 1A
FIG. 1B
FIG. 1C

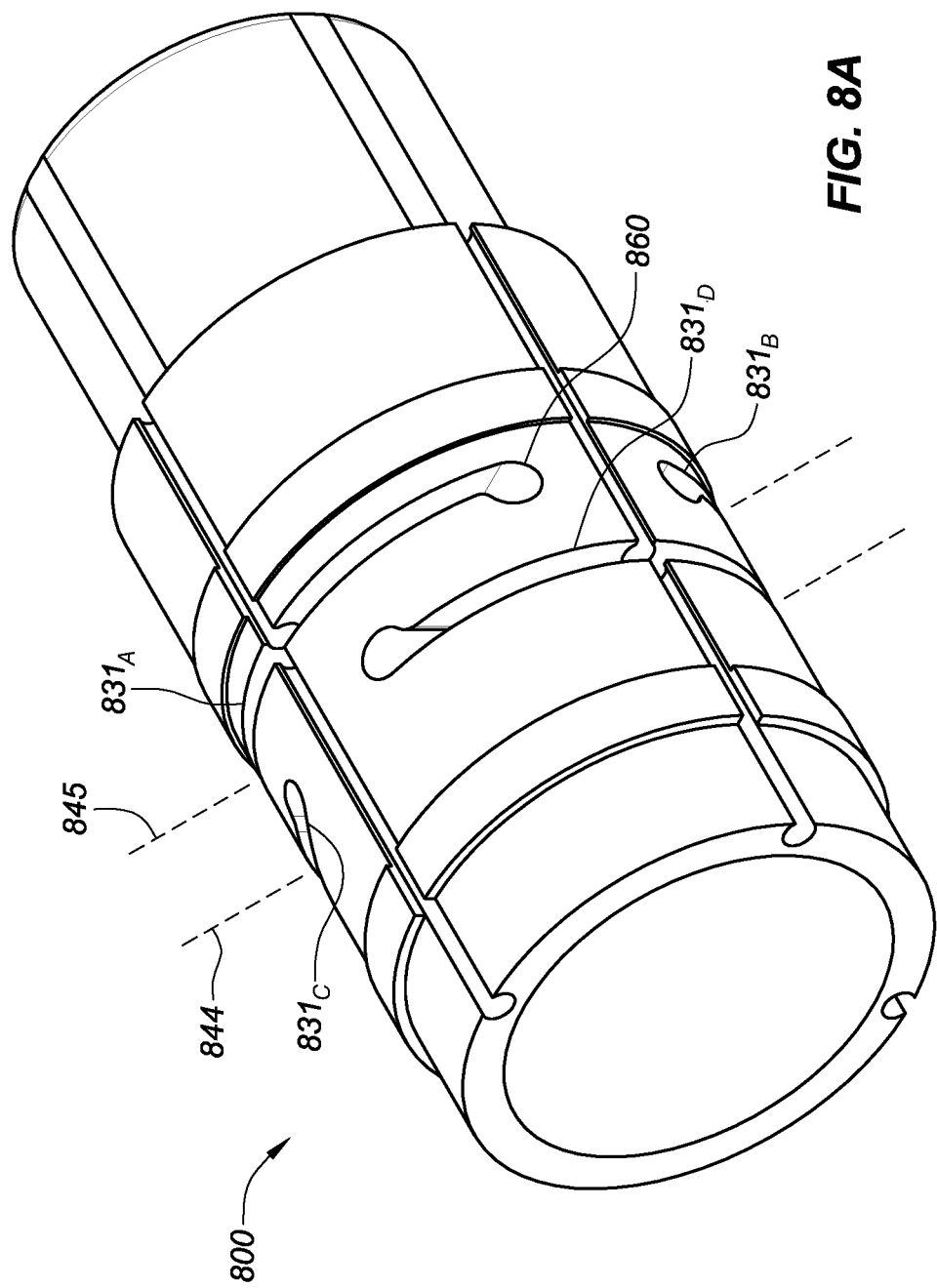

FORCE SENSING CATHETER SYSTEM

CROSS-REFERENCE TO RELATED APPLICATIONS

This application claims the benefit of U.S. provisional application No. 62/653,210, filed 5 Apr. 2018, which is hereby incorporated by reference as though fully set forth herein.

BACKGROUND a. Field

The instant disclosure relates to various types of medical catheters, in particular catheters for diagnostics within, and/or treatment of, a patient's cardiovascular system. In one embodiment, the instant disclosure relates to an ablation catheter for treating cardiac arrhythmias within a cardiac muscle. More specifically, the instant disclosure relates to force sensing systems capable of determining a force applied at a distal tip of a catheter.

b. Background Art

Exploration and treatment of various organs or vessels has been made possible using catheter-based diagnostic and treatment systems. These catheters may be introduced through a vessel leading to the cavity of the organ to be explored, and/or treated. Alternatively, the catheter may be introduced directly through an incision made in the wall of the organ. In this manner, the patient avoids the trauma and extended recuperation times typically associated with open surgical procedures.

The human heart routinely experiences electrical currents traversing its many layers of tissue. Just prior to each heart contraction, the heart depolarizes and repolarizes as electrical currents spread across the heart. In healthy hearts, the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization waves become chaotic.

Catheters are used in a variety of diagnostic and/or therapeutic medical procedures to diagnose and correct conditions such as atrial arrhythmia. Typically, in such a procedure, a catheter is manipulated through a patient's vasculature to the patient's heart carrying one or more end effectors which may be used for mapping, ablation, diagnosis, or other treatment. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess pressure between the ablation catheter tip and the targeted myocardial tissue may result in excessive ablation which may permanently damage the cardiac muscle and/or surrounding nerves. When the contact pressure between the ablation catheter tip and the targeted myocardial tissue is below a target pressure, the efficacy of the ablation therapy may be reduced.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact pressure between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation.

Mapping systems often rely on manual feedback of the catheter and/or impedance measurements to determine when the catheter is properly positioned in a vessel or organ. Mapping systems do not consider contact force with the vessel or organ wall that may modify the true wall location. Accordingly, the mapping may be inaccurate due to artifacts created due to excessive contact forces between the catheter and vessel/organ wall.

To facilitate improved mapping, it is desirable to detect and monitor contact forces between a catheter tip and a wall of an organ/vessel to permit more accurate mapping.

In view of the foregoing, it would be desirable to provide a catheter-based diagnostic and/or treatment system that permits sensing of the load applied to a distal tip of the catheter.

The foregoing discussion is intended only to illustrate the present field and should not be taken as a disavowal of claim scope.

BRIEF SUMMARY

The instant disclosure relates to various types of medical catheters. More specifically, the instant disclosure relates to electrophysiology catheters including a deformable body for accurately detecting a force exerted on a distal tip of the catheter.

Aspects of the present disclosure are directed toward systems and methods for detecting force applied to a distal tip of a medical catheter using a fiber-optic force sensor and processor circuitry. In particular, the instant disclosure relates to a deformable body near a distal tip of the medical catheter that deforms in response to the force applied at the distal tip. The fiber-optic force sensor detects various components of the deformation, and the processor circuitry, based on the detected components of the deformation, determines a force applied to the distal tip of the catheter.

Various embodiments of the present disclosure are directed to force-sensing catheter systems. In one such embodiment, a force-sensing catheter system is disclosed including a catheter tip coupled to a deformable body. The deformable body deforms in response to a force exerted on the catheter tip. The deformable body includes an annulus, four flexure portions, and three optical fiber grooves. The annulus has inner and outer surfaces. Each of the four flexure portions extend from the outer surface to the inner surface of the annulus. Each of the three optical fiber grooves extend along the outer surface of the annulus, parallel to a longitudinal axis of the annulus, and across at least one of the four flexure portions. In more specific embodiments, the force-sensing catheter system further includes a measurement system and processor circuitry. The measurement system is coupled to the deformable body, and includes three sensing elements coupled to respective optical fiber grooves. Each of the sensing elements detect the deformation of the deformable body across the flexure portions, in response to the force exerted on the catheter tip, and transmit a signal indicative of the sensed deformation. The processor circuitry is communicatively coupled to the measurement system, and receives the signals from each of the sensing elements, indicative of the deformation, and determines a magnitude of the force exerted on the catheter tip.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which:

FIG. 1A is a block diagram of a force sensing system, consistent with various embodiments of the present disclosure;

FIG. 1B is a schematic depiction of an interferometric fiber optic sensor, consistent with various embodiments of the present disclosure;

FIG. 1C is a schematic depiction of a fiber Bragg grating optical strain sensor, consistent with various embodiments of the present disclosure;

FIG. 8A is an isometric side view of a deformable body, consistent with various embodiments of the present disclosure;

Figure 1:
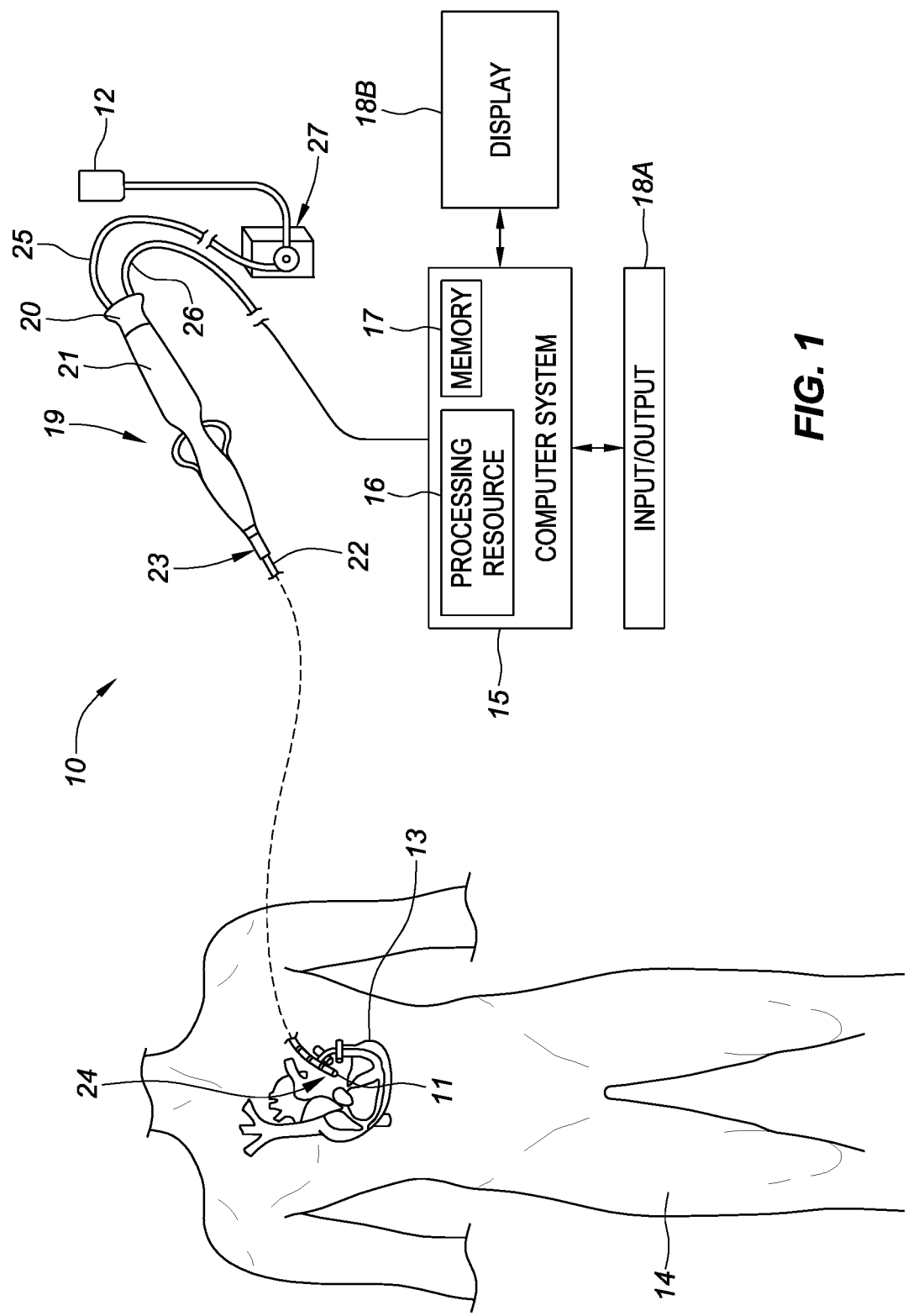
FIG. 1 is a diagrammatic overview of a system for force sensing, consistent with various embodiments of the present disclosure.

While various embodiments discussed herein are amenable to modifications and alternative forms, aspects thereof have been shown by way of example in the drawings and will be described in further detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION OF EMBODIMENTS

Aspects of the present disclosure are directed toward systems and methods for detecting force applied to a distal tip of a medical catheter. In particular, the instant disclosure relates to a force sensing medical catheter including a deformable body near a distal tip that deforms in response to the force applied. Sensors, such as fiber-optic sensors, detect various components of the deformation, and processor circuitry, based on the detected components of the deformation, determines a force applied to the distal tip of the catheter. Importantly, various aspects of the present disclosure are directed to electrophysiology catheters including a deformable body and a flexible ablation tip.

Optical force sensing systems have previously incorporated deformable bodies to provide a clinician with additional distal tip feedback during administration of a therapy or diagnostic procedure, for example.

Various embodiments of the present disclosure are directed to a catheter force sensing system including a deformable body for detecting a force exerted on a distal tip of the catheter. Force sensing systems as disclosed herein may be calibrated to measure forces exerted on a distal tip of a medical catheter via fiber optic measurement of a deformation of the deformable body. Such a force sensing system may be particularly useful for cardiovascular ablation catheters, where a distal tip of the catheter is positioned in contact with myocardial tissue that is to receive an ablation therapy and necrose in response to the treatment. Ablation therapy can be a useful treatment for patients with a cardiac arrhythmia (e.g., atrial fibrillation). The necrosed tissue facilitates electrical isolation of unwanted electrical impulses often emanating from pulmonary veins (and arrhythmic foci). By electrically isolating the electrica impulses from the left atrium of the cardiac muscle, for example, the symptoms of atrial fibrillation can be reduced or eliminated. To the extent that arrhythmic foci are located within a tissue ablation zone, the arrhythmic foci are destroyed.

In a typical ablation therapy for atrial fibrillation, pulmonary veins are treated with an ablation therapy to isolate arrhythmic foci within the pulmonary veins from a cardiac muscle. The arrhythmic foci are known for emitting stray electrical signals which may impede the proper pumping functionality of the cardiac muscle. A distal tip of the catheter may include electrophysiology electrodes (also referred to as spot electrodes) which help to expedite diagnosis and treatment of a source of a cardiac arrhythmia, and may also be used to confirm a successful ablation therapy by determining the isolation of the arrhythmic foci from the left atrium, for example, or the destruction of the arrhythmic foci entirely.

During an ablation therapy, a distal end of an ablation catheter tip contacts ablation targeted myocardial tissue in order to conductively transfer energy (e.g., radio-frequency, thermal, etc.) thereto. It has been discovered that consistent force, during a series of tissue ablations, forms a more uniform and transmural lesion line. Uniform lesion lines exhibit improved isolation of electrical impulses produced by arrhythmic foci, thereby improving the overall efficacy of the ablation therapy. To achieve such consistent force, aspects of the present disclosure utilize a deformable body in the ablation catheter tip. The deformable body deforms in response to forces being exerted upon a distal end of the ablation catheter tip. The deformation of the deformable body may then be measured by a measurement device (e.g., ultrasonic, magnetic, optical, interferometry, etc.). Various embodiments of the present disclosure are directed to a deformable body used in combination with an optical measurement system. Based on the tuning of the deformable body and/or the calibration of the measurement device, the deformation may then be associated with a force exerted on the distal end of the ablation catheter tip (e.g., via a lookup table, formula(s), calibration matrix, etc.). Processor circuitry may be used to determine the exerted force, and output a signal indicative of the force exerted on the catheter tip. The calculated force may then be displayed to a clinician, stored in memory, or otherwise communicated. For example, haptic feedback can be utilized in the catheter handle to indicate proper or insufficient contact force with the targeted myocardial tissue. In some specific embodiments, the processor circuitry may intervene in the ablation therapy where the force exerted on the tissue by the catheter tip is too low or high.

Various embodiments of the present disclosure are directed to a deformable body for a flexible ablation catheter tip assembly for intravascular catheter applications. While rigid tip catheters transfer loads exerted on the tip to the deformable body in a fairly consistent manner, flexible tips (e.g., the flexible ablation tip used on St. Jude Medical Inc.'s FlexAbility™ Irrigated Ablation Catheter) add variability to the loading path between the tip and deformable body due to its flexible nature. Aspects of the present disclosure are directed to improved deformable bodies which maintain force sensing accuracy of the deformable body when used in conjunction with a flexible ablation tip.

Details of the various embodiments of the present disclosure are described below with specific reference to the figures.

Referring now to the drawings wherein like reference numerals are used to identify identical components in the various views, FIG. 1 generally illustrates a system 10 for force detecting having an elongated medical device 19 that includes a sensor assembly 11 (e.g., fiber optic based distance measurement sensor) configured to be used in a body 14 for medical procedures. The elongated medical device 19 may be used for diagnosis, visualization, and/or treatment of tissue 13 (such as cardiac or other tissue) in the body. For example, the medical device 19 may be used for ablation therapy of tissue 13 or mapping purposes in the patient's body 14. FIG. 1 further shows various sub-systems included in the overall system 10. The system 10 may include a main computer system 15 (including an electronic control unit 16 ("processing resource" or controller circuitry) and data storage 17, e.g., memory). The computer system 15 may further include conventional interface components, such as various user input/output mechanisms 18A and a display 18B, among other components. Information provided by the sensor assembly 11 may be processed by the computer system 15 and may provide data to the clinician via the input/output mechanisms 18A and/or the display 18B, or in other ways as described herein. Specifically, the display 18B may visually communicate a force exerted on the elongated medical device 19—where the force exerted on the elongated medical device 19 is detected in the form of a deformation of at least a portion of the elongated medical device by the sensor assembly 11, and the measured deformations are processed by the computer system 15 to determine the force exerted.

In the illustrative embodiment of FIG. 1, the elongated medical device 19 may include a cable connector or interface 20, a handle 21, a tubular body or shaft 22 having a proximal end 23 and a distal end 24. The elongated medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongated medical device 19.

The handle 21 provides a portion for a user to grasp or hold the elongated medical device 19 and may further provide a mechanism for steering or guiding the shaft 22 within the patient's body 14. For example, the handle 21 may include a mechanism configured to change the tension on a pull-wire extending through the elongated medical device 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the sensor assembly 11. For example, if contact to tissue 13 is made by distal tip 24, the sensor assembly 11 will transmit data to the computer system 15 indicative of contact. In response to the computer system 15 determining that the data received from the sensor assembly 11 is indicative of a contact between the distal tip 24 and tissue 13 within a patient's body 14, the computer system 15 may operate a light-emitting-diode on the handle 21, a tone generator, a vibrating mechanical transducer, and/or other indicator(s), the outputs of which could vary in proportion to the calculated contact force.

The computer system 15 may utilize software, hardware, firmware, and/or logic to perform a number of functions described herein. The computer system 15 may be a combination of hardware and instructions to share information. The hardware, for example may include processing resource 16 and/or a memory 17 (e.g., non-transitory computer-readable medium (CRM) database, etc.). A processing resource 16, as used herein, may include a number of processors capable of executing instructions stored by the memory resource 17. Processing resource 16 may be integrated in a single device or distributed across multiple devices. The instructions (e.g., computer-readable instructions (CRI)) may include instructions stored on the memory 17 and executable by the processing resource 16 for force detection.

The memory resource 17 is communicatively coupled with a processing resource 16. The memory 17, as used herein, may include a number of memory components capable of storing instructions that are executed by the processing resource 16. The memory 17 may be a non-transitory computer readable storage medium, for example. The memory 17 may be integrated in a single device or distributed across multiple devices. Further, the memory 17 may be fully or partially integrated in the same device as the processing resource 16 or it may be separate but accessible to that device and the processing resource 16. Thus, it is noted that the computer system 15 may be implemented on a user device and/or a collection of user devices, on a mobile device and/or a collection of mobile devices, and/or on a combination of the user devices and the mobile devices.

Memory 17 may be communicatively coupled with processing resource 16 via a communication link (e.g., path). The communication link may be local or remote to a computing device associated with the processing resource 16. Examples of a local communication link may include an electronic bus internal to a computing device where the memory 17 is one of a volatile, non-volatile, fixed, and/or removable storage medium in communication with the processing resource 16 via the electronic bus.

In various embodiments of the present disclosure, computer system 15 may receive optical signals from a sensor assembly 11 via one or more optical fibers extending a length of catheter shaft 22. A processing resource 16 of the computer system 15 may execute an algorithm stored in memory 17 to compute a force exerted on catheter tip 24, based on the received optical signals.

U.S. Pat. No. 8,567,265 discloses various optical force sensors for use in medical catheter applications, such optical force sensors are hereby incorporated by reference as though fully disclosed herein.

FIG. 1A is a block diagram of a force sensing system 70, consistent with various embodiments of the present disclosure. The force sensing system 70 may comprise an electromagnetic source 72, a coupler 74, a receiver 76, an operator console 77 operatively coupled with a controller circuitry 78 and a storage device 79. The electromagnetic source 72 transmits electromagnetic radiation 80 (photons) that is substantially steady state in nature, such as a laser or a broadband light source. A transmission line 82 such as a fiber optic cable carries the radiation 80 to the coupler 74, which directs the radiation 80 through a transmitting/receiving line 84 and through a fiber optic element contained within a flexible, elongated catheter assembly 87 to a fiber optic force sensing element 90 within a sensor assembly 11. It is to be understood that while various embodiments of the present disclosure are directed to sensing systems with fiber optic force sensing elements for detecting a change in dimension (e.g., deformation) of a catheter assembly 87, various other embodiments may include non-fiber optic based measurement systems as are well known in the art. Moreover, it is to be understood that the sensing elements measure the deformation of a deformable body (e.g., a distance or displacement), and do not directly measure a force. The catheter assembly 87 may include one or more transmitting/receiving lines 84 coupled to one or more fiber optic elements 83 (as shown in FIGS. 1B-C) within the sensor assembly 11. The fiber optic element(s) 83 of the catheter assembly 87 and transmitting/receiving line(s) 84 may be coupled through a connector 86 as depicted in FIG. 1A.

The catheter assembly 87 may have a width and a length suitable for insertion into a bodily vessel or organ. In one embodiment, the catheter assembly 87 comprises a proximal portion 87a, a middle portion 87b and a distal portion 87c. The distal portion 87c may include an end effector which may house the sensor assembly 11 and the one or more fiber optic sensing element(s) 90. The catheter assembly may be of a hollow construction (i.e. having a lumen) or of a non-hollow construction (i.e. no lumen), depending on the application.

In response to a deformation of a deformable body, due to a force being exerted on a distal tip of a catheter, one or more fiber optic elements 83 (as shown in FIGS. 1B-C) within the sensor assembly 11 will modulate the radiation received from the transmission line 82 and transmit the modulated radiation to the operator console 77 via receiving line 84. Once the radiation is received by the operator console 77, controller circuitry (e.g., microprocessor) 78 may run an algorithm stored on storage device 79 to determine a distance across the sensing element(s) 90 and associate the distance with a force exerted on the catheter tip.

A fiber optic sensing element 90 for detecting a deformation of a deformable body may be an interferometric fiber optic strain sensor, a fiber Bragg grating strain sensor, or other fiber optic sensor well known in the art.

Referring to FIG. 1B, fiber optic sensing element 88 is an interferometric fiber optic strain sensor 90a. In this embodiment, the transmitted radiation 80 enters an interferometric gap 85 within the interferometric fiber optic strain sensor 90a. A portion of the radiation that enters the interferometric gap 85 is returned to the fiber optic cable 87c as a modulated waveform 89a. The various components of the interferometric fiber optic strain sensor 90 may comprise a structure that is integral with the fiber optic element 83. Alternatively, the fiber optic element 83 may cooperate with the structure to which it is mounted to form the interferometric gap 85.

Referring to FIG. 1C, fiber optic sensing element 90, of FIG. 1A, is a fiber Bragg grating strain sensor 90b. In this embodiment, the transmitted radiation 80 enters a fiber Bragg grating 90b, the gratings of which are typically integral with the fiber optic element 83 and reflect only a portion 89b of the transmitted radiation 80 about a central wavelength λ. The central wavelength λ at which the portion 89b is reflected is a function of the spacing between the gratings of the fiber Bragg grating. Therefore, the central wavelength λ is indicative of the strain on the fiber Bragg grating strain sensor 90b relative to some reference state.

The reflected radiation 89, be it the modulated waveform 89a (as in FIG. 1B) or the reflected portion 89b (as in FIG. 1C), is transmitted back through the transmitting/receiving line 84 to the receiver 76. The force sensing system 70 may interrogate the one or more fiber optic strain sensing element(s) 90 at an exemplary and non-limiting rate of 10-Hz. The receiver 76 is selected to correspond with the type of strain sensing element 90 utilized. That is, the receiver may be selected to either detect the frequency of the modulated waveform 89a for use with the interferometric fiber optic strain sensor 90a, or to resolve the central wavelength of the reflected portion 89b for use with fiber Bragg grating strain sensor 90b. The receiver 76 manipulates and/or converts the incoming reflected radiation 89 into digital signals for processing by the controller circuitry 78.

Figure 2A:
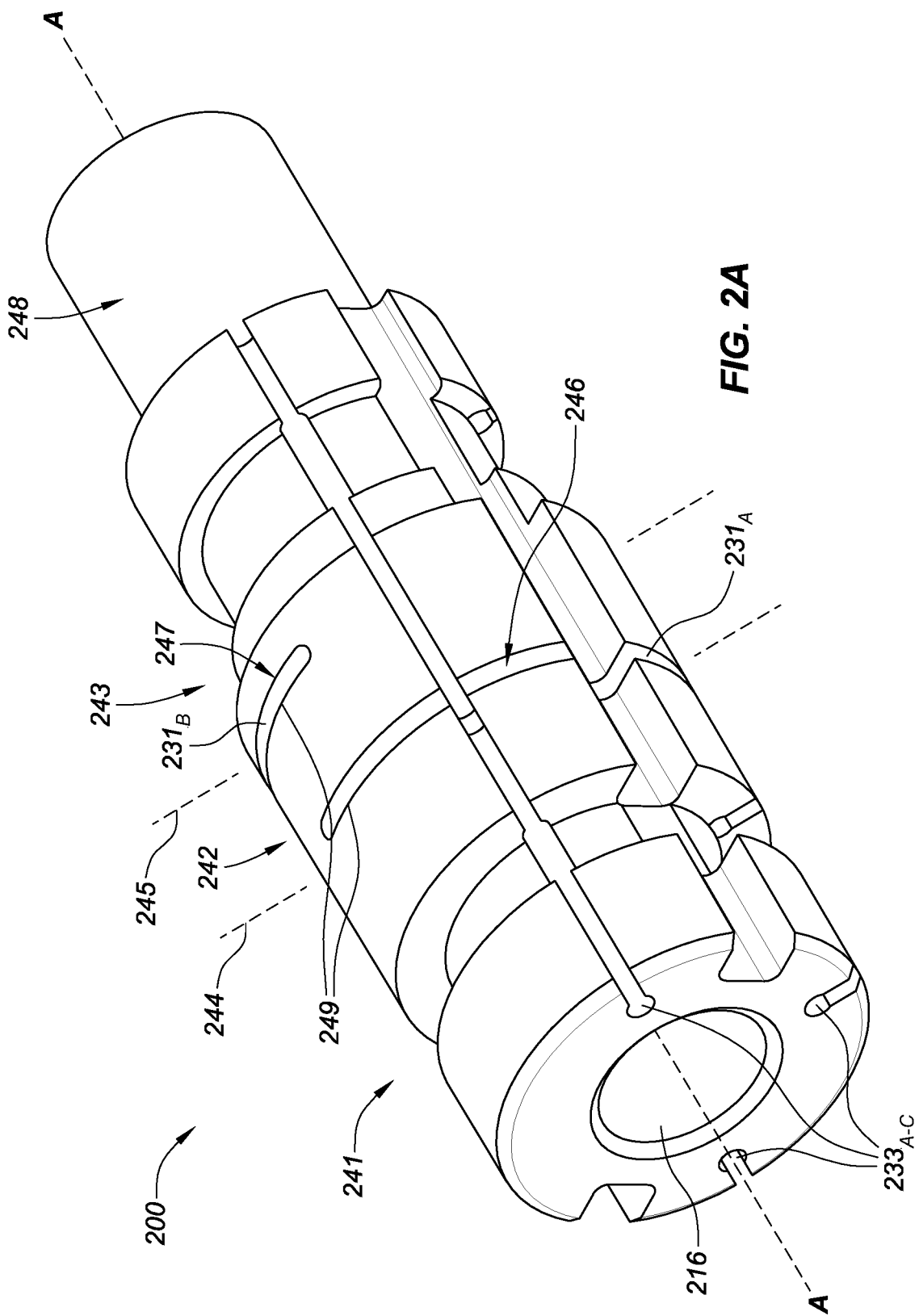
FIG. 2A is an isometric side view of a deformable body, consistent with various embodiments of the present disclosure.

FIG. 2A is an isometric side view of a deformable body 200 for a force sensing catheter system, consistent with various embodiments of the present disclosure. The deformable body 200 is designed to house a plurality of fiber optic cables that extend through grooves $233_{A-C}$. In the present embodiment, the deformable body 200 is divided into a plurality of segments along a longitudinal axis A-A. The segments 241, 242, and 243 are bridged by flexure portions $231_{A-B}$, each flexure portion defines neutral planes 244 and 245. Each of the neutral planes constitute a location within the respective flexure portions where the stress is zero when subjected to a pure bending moment in any direction.

In some embodiments, adjacent members of the segments 241, 242, and 243 may define a plurality of gaps 246 and 247 at the flexure portions $231_{A-B}$, each having a separation dimension. It is noted that while the longitudinal separation dimensions of the gaps are depicted as being uniform, the separation dimensions may vary across a given gap, or between gaps. Moreover, the radial dimension of the gaps may also vary (e.g., to compensate for the effects of a moment exerted along a length of the deformable body 200).

Deformable body 200 includes a plurality of grooves $233_{A-C}$ that are formed within an outer surface 248. The grooves 233 may be spaced rotationally equidistant (i.e. spaced 90° apart where there are three grooves) about a longitudinal axis A-A, and may be oriented parallel with the longitudinal axis. Each of the grooves may terminate at a respective one of the gaps 246 and 247 of the flexure portions $231_{A-B}$. For example, a groove 233 may extend along a proximal segment 243 and intermediate segment 242 terminating at gap 246 of flexure portion $231_A$. Other grooves may extend along the proximal segment 243 terminating at gap 247 of flexure portion $231_B$.

When the deformable body 200 is used in conjunction with a fiber optic distance measurement sensor, fiber optic cables may be disposed in grooves $233_{A-C}$ such that the distal ends of the fiber optic cables terminate at the gaps 246 and 247 of either flexure portion $231_{A-B}$. For example, a first fiber optic cable may extend along groove $233_A$, terminating proximate or within the gap 246 of flexure portion $231_A$. Likewise, a second fiber optic cable may extend along a second groove 233 and terminate proximate or within the gap 247 of flexure portion $231_B$. Surfaces 249 of the flexure portions $231_{A-B}$, opposite the distal ends of first and second fiber optic cables, may be coated with a highly reflective material, or third and fourth fiber optics with mirrored surfaces positioned opposite the first and second fiber optics, relative to the gaps 246 and 247. Alternatively, a fiber Bragg grating strain sensor may be implemented across the gaps.

Gaps 246 and 247 at flexure portions $231_{A-B}$ may be formed so that they extend laterally through a major portion of deformable body 200. For example, the gaps may extend into an irrigant lumen 216. Also, the gaps may be oriented to extend substantially normal to a longitudinal axis A-A of the deformable body 200, or at an acute angle with respect to the longitudinal axis. In the depicted embodiment, the deformable body 200 comprises a hollow cylindrical tube (e.g., annulus) with the gaps 246 and 247 extending transverse to the longitudinal axis from an outer surface 248 to the irrigant lumen 216.

When the deformable body 200 is integrated into an ablation catheter tip assembly, a force exerted on the tip causes the deformation of one or more of the gaps 246 and 247. The change in the gaps are measured by the optical measurement system and controller circuitry associates the deformation of the deformable body with a force exerted on the tip (based on a calibration matrix, for example).

In some embodiments, electrical discharge machining ("EDM") may be used to form grooves $233_{A-C}$ and flexure portions $231_{A-B}$.

Assembled optical force sensors including deformable body 200 of FIG. 2A, when calibrated properly, are capable of detecting a force exerted on the catheter tip to the gram. However, due to the placement of the optical fibers circumferentially along outer surface 248 of the deformable body, the relative weighting of measurements from the respective optical fibers may not be even. This is due in part to two of the optical fibers measuring a deformation across the same gap. These two optical fibers will report similar distances. Moreover, the uneven measurement weighting is associated with the optical fibers being circumferentially distributed 90 degrees apart from one another along the outer surface 248. This configuration results in approximately 30 degree phase shift of the two optical fibers sharing the same gap under lateral loading of the catheter tip (as shown in reference to FIG. 3). Accordingly, a force calculation for this configuration would not equally weight the displacement measurement of each optical fiber the same, and this weighting may further vary based on the relative orientation of the applied load. For example, a first and second optical fiber may be heavily weighted in response to a pure axial loading, while a third optical fiber may be lightly weighted in the force calculation. As a result, any noise injected into the force calculation by the first or second optical fiber may increase the resulting error in the force determination.

The following embodiments are directed to further improving force determination accuracy of an optical force measurement system by improving the balance of a deformable body therein.

Figure 2B:
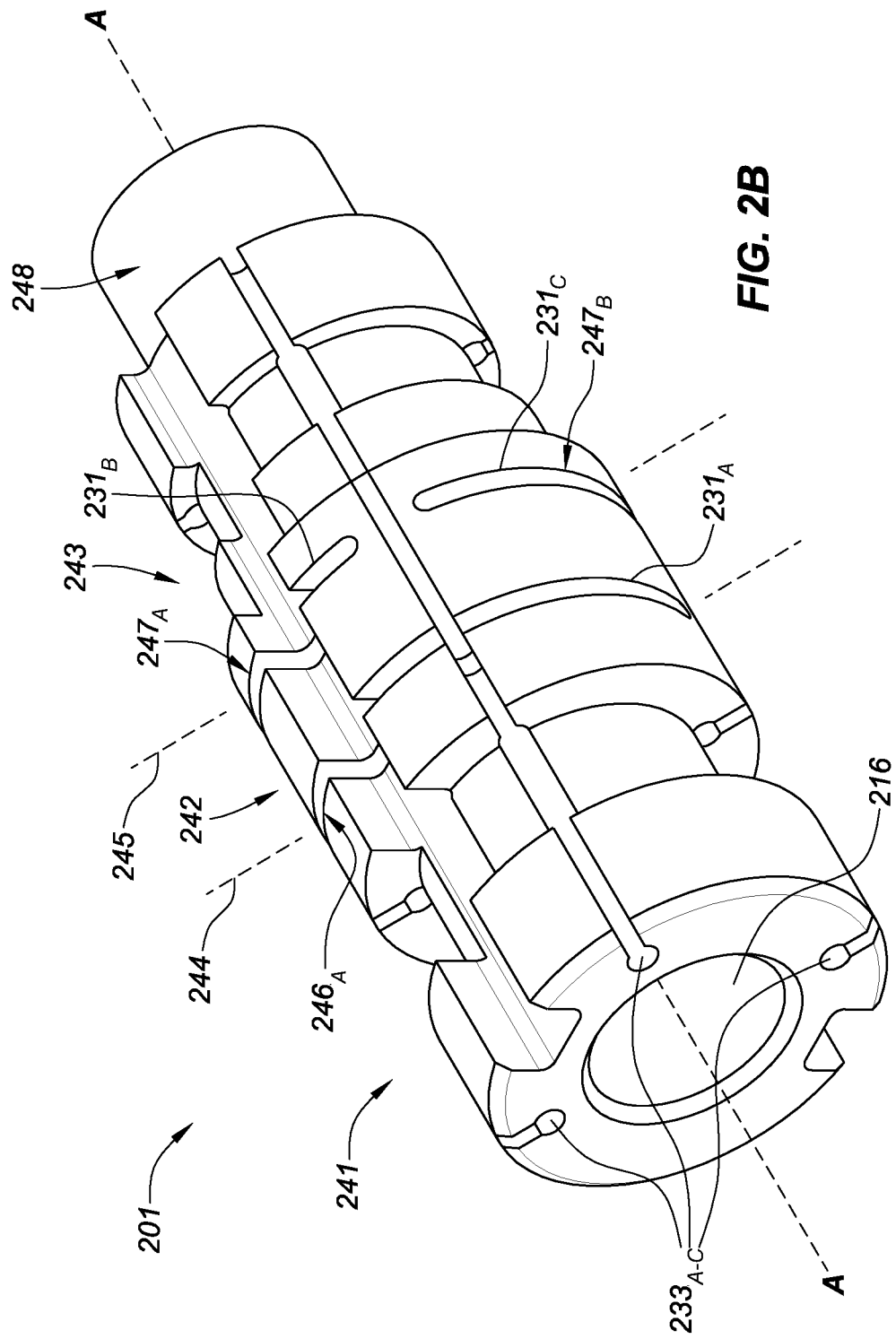
FIG. 2B is an isometric side view of a deformable body, consistent with various embodiments of the present disclosure.

FIG. 2B is an isometric side view of a deformable body 201, consistent with various embodiments of the present disclosure. The deformable body 201 is designed to house a plurality of fiber optic cables that extend through grooves $233_{A-C}$. In the present embodiment, the deformable body 201 is divided into a plurality of segments along a longitudinal axis A-A. The segments 241, 242, and 243 are bridged by flexure portions $231_{A-D}$, two flexure portions define each neutral plane 244 and 245. Though not shown in FIG. 2B, flexure portion $231_A$ has a mirrored (across a longitudinal axis A-A) flexure portion $231_D$, both of which are co-planar with neutral plane 244.

In some embodiments, adjacent members of the segments 241, 242, and 243 may define a plurality of gaps $246_{A-B}$ and $247_{A-B}$ at the flexure portions $231_{A-D}$, each having a separation dimension. It is noted that while the longitudinal separation dimensions of the gaps are depicted as being uniform, the separation dimensions may vary across a given gap, or between gaps. Moreover, the radial dimension of the gaps may also vary (e.g., to compensate for the effects of a moment exerted along a length of the deformable body 201).

Deformable body 201 includes a plurality of grooves $233_{A-C}$ that are formed within an outer surface 248. Similar to the embodiment of FIG. 2A, the grooves 233 may be spaced rotationally equidistant (i.e. spaced 90° apart where there are three grooves) about a longitudinal axis A-A, and may be oriented parallel with the longitudinal axis. Each of the grooves may terminate at a respective one of the gaps $246_{A-B}$ and $247_{A-B}$ of the flexure portions $231_{A-D}$. For example, a first groove $233_A$ may extend along a proximal segment 243 and intermediate segment 242 terminating at gap $246_A$ of flexure portion $231_A$. A second groove $233_B$ may extend along the proximal segment 243 terminating at gap $247_B$ of flexure portion $231_C$. A third groove $233_C$ may extend along the proximal segment 243 terminating at gap $247_A$ of flexure portion $231_B$.

The four flexure portions $231_{A-D}$, in combination with three optical fibers within the grooves $233_{A-C}$, facilitate improved measurement independence between the respective optical fibers as each of the optical fibers are measuring a deformation across a unique gap. As discussed in more detail in regard to FIG. 5, aspects of the present disclosure improve theta angle for an applied load across a deformable body as measured by three optical fiber. Theta angle is defined as the relative angle of a lateral force vector to a plane extending coincident to a longitudinal axis A-A of a catheter.

Gaps $246_{A-B}$ and $247_{A-B}$ at flexure portions $231_{A-D}$ may be formed so that they extend laterally through a major portion of deformable body 201. For example, the gaps may extend into an irrigant lumen 216. Also, the gaps may be oriented to extend substantially normal to a longitudinal axis A-A of the deformable body 201, or at an acute angle with respect to the longitudinal axis. In the depicted embodiment, the deformable body 201 comprises a hollow cylindrical tube with the gaps $246_{A-B}$ and $247_{A-B}$ extending transverse to the longitudinal axis from a surface 248 to the irrigant lumen 216.

As shown in FIGS. 2A and 2B, flexure portions $231_{A-B\ (C-D)}$ define semi-circular segments that intercept an inner diameter of deformable body 200/201. The radial depth of the gaps 246 and 247 can be tuned to establish a desired flexibility of the various flexure portions 231. That is, the greater the depth of the flexure portions 231 the more flexible the flexure portions are. The flexure portions 231 may be formed by the various ways available to the artisan, such as but not limited to sawing, machining, laser cutting or EDM. The gaps $246_{A-B}$ and $247_{A-B}$ which form the flexure portions $231_{A-D}$ may be formed to define non-coincident neutral planes. The shape of the flexure portions 231, distance between the flexure portions, and the depth of the flexure portions further dictate the maximum stress that the deformable body 200/201 is capable of absorbing before plastically deforming.

When a fiber optic measurement system consistent with the above is assembled, one or more fiber optic cables are mechanically coupled to deformable body 200/201 via grooves 233. In some embodiments, each of the fiber optics may be communicatively coupled to a Fabry-Perot strain sensor within one of the gaps 246 and 247 which form the flexure portions 231. The Fabry-Perot strain sensor includes transmitting and reflecting elements to define an interferometric gap. The free end of the reflecting element may be faced with a semi-reflecting surface.

In some embodiments of a fiber optic measurement system, the fiber optic cables may be positioned along the grooves $233_{A-C}$ so that the respective Fabry-Perot strain sensor is bridged across one of the flexure portions 231. For example, a fiber optic cable may be positioned within groove $233_A$ so that the Fabry-Perot strain sensor bridges the gap at flexure portion $231_B$ between distal and intermediate segments, 241 and 242, respectively, of deformable body 200/201.

In some embodiments, deformable body 200/201 may comprise a composition including a stainless steel alloy (or other metal alloy with characteristics including a high tensile strength, e.g., titanium).

In response to a force exerted on a distal tip, deformable body 200/201 deforms. The amount deformable body 200/201 deforms is directly correlated to a force exerted on a catheter tip coupled to the deformable body.

Figure 3:
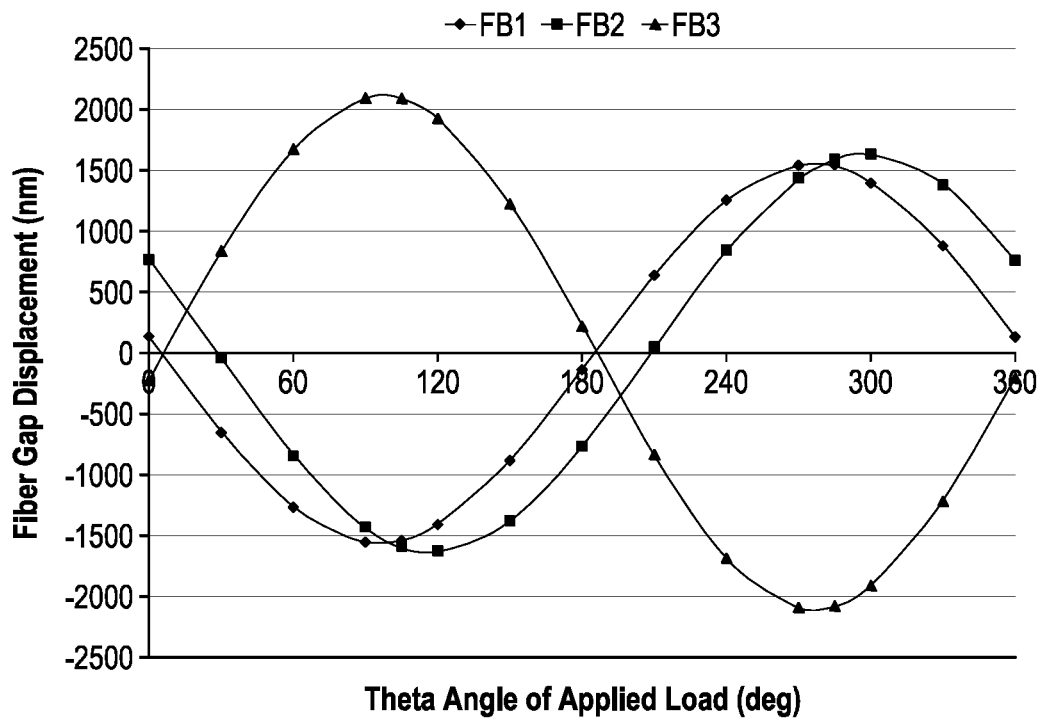
FIG. 3 is a graph charting theta angle of an applied load vs. fiber gap displacement as simulated for the deformable body of FIG. 2A, consistent with various embodiments of the present disclosure.

FIG. 3 is a graph charting theta angle of an applied load vs. fiber gap displacement as simulated for the deformable body of FIG. 2A, consistent with various embodiments of the present disclosure. As shown in FIG. 3, while fiber optics 1 and 2 ("FB1" and "FB2," respectively) are physically located 90 degrees apart longitudinal axis A-A, their reported displacement data is only phase-offset by approximately 30 degrees because they are both located on the same flexure element. The small phase offset between fiber optics 1 and 2 minimize the relative value of each measurement which may result in undesirably high force measurement error (in some force applications when used in conjunction with various catheter tip designs).

The finite element analysis simulation charted in FIG. 3 is a 50 gram force laterally loaded in 30 degree increments circumferentially around the catheter tip.

Figure 4:
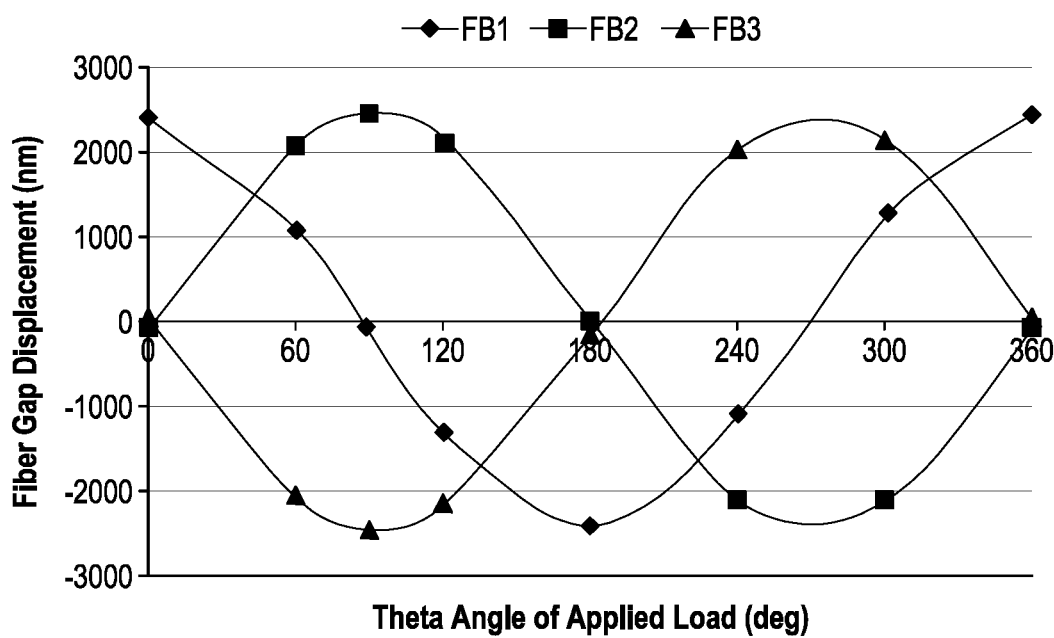
FIG. 4 is a graph charting theta angle of an applied load vs. fiber gap displacement as simulated for the deformable body of FIG. 2B, consistent with various embodiments of the present disclosure.

FIG. 4 is a graph charting theta angle of an applied load vs. fiber gap displacement as simulated for the deformable body of FIG. 2B, consistent with various embodiments of the present disclosure. As shown in FIG. 4, the four flexure portion design of deformable body 201 shows improved phase-offset balance between each of the fiber optics—approximately 90 degrees between each of the fiber optics.

The finite element analysis simulation charted in FIG. 4 is a 50 gram force laterally loaded in 30 degree increments circumferentially around the catheter tip.

Figure 5A:
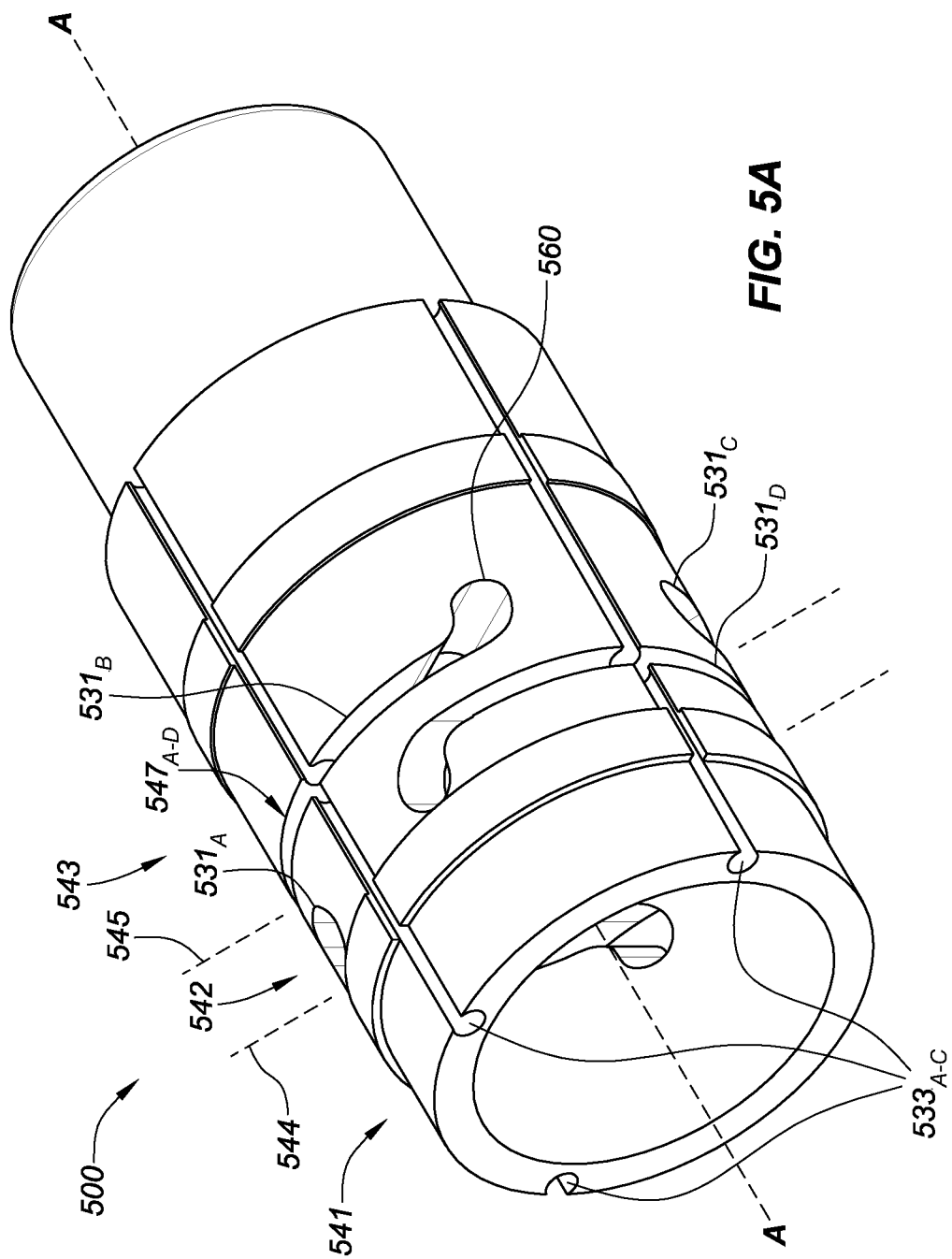
FIG. 5A is an isometric side view of a deformable body, consistent with various embodiments of the present disclosure.

FIG. 5A is an isometric side view of a deformable body 500, consistent with various embodiments of the present disclosure. The deformable body 500 is designed to house a plurality of fiber optic cables that extend through grooves $533_{A-C}$. In the present embodiment, the deformable body 500 is divided into a plurality of segments along a longitudinal axis A-A. The segments 541, 542, and 543 are bridged by flexure portions $531_{A-D}$, two flexure portions define each neutral plane 544 and 545. In some embodiments, adjacent members of the segments 541, 542, and 543 may define a plurality of gaps $547_{A-D}$ at the flexure portions $531_{A-D}$, each having a separation dimension.

Deformable body 500 includes a plurality of grooves $533_{A-C}$, which may be spaced circumferentially distributed about a longitudinal axis A-A, and may be oriented parallel with the longitudinal axis. Each of the grooves may terminate at a respective one of the gaps $547_{A-D}$ of the flexure portions $531_{A-D}$. The four flexure portions $531_{A-D}$, in combination with three optical fibers within the grooves $533_{A-C}$, facilitate improved measurement independence between the respective optical fibers as each of the optical fibers are measuring a deformation across a unique gap.

When assembled in a partial ablation catheter tip assembly, deformable body 500 may be coupled at a distal end to a flexible ablation tip and at a proximal end to a catheter shaft that extends to a catheter handle. The deformable body 500 is designed in such a way as to receive forces exerted on the flexible tip and to absorb such force by deflecting and deforming in response thereto. Further, the deformable body 500 may be outfitted with a measurement device which facilitates measurement of the deflection/deformation which may be correlated with the force exerted on the flexible tip and communicated with a clinician. Knowledge of a force exerted on the flexible tip may be useful for a number of different cardiovascular operations; for example, during a myocardial tissue ablation therapy it is desirable to know a contact force exerted by the flexible tip on target tissue as the time to necrose tissue is based on energy transferred between the catheter and tissue—which is highly dependent upon the extent of tissue contact.

Embodiments of the present disclosure may utilize a fiber optic based measurement system to measure the deformation of deformable body 500. Fiber optic cables may be coupled to grooves $533_{A\text{-}C}$ along an outer diameter of deformable body 500. Accordingly, a light source may be applied to one or more of the fiber optic cables and a time-of-flight measurement may be recorded for one or more wave-lengths of light to cross a gap between the fiber-optic pairs in flexure portions $531_{A\text{-}D}$. In various embodiments, the fiber optic cables run proximally along a shaft to a catheter handle, which may include processor circuitry or be communicatively coupled to the processor circuitry. The sensed time-of-flight across the flexure portions 531 may be associated with a deflection of the deformable body from a static state. During calibration, the deformable body 500 may be tested to determine a calibration matrix which associates deformation of the structural member with an applied-force at a flexible tip. Where the fiber optic based measurement system is a Fabry-Perot sensor, a phase change of light extending across the gap is indicative of a deformation of the deformable body.

Each flexure portion $531_{A\text{-}D}$ of deformable body 500 includes a pair of strain reliefs 560 at either end. These strain reliefs facilitate desirable deformation characteristics of the flexure portions such as improved deformation in response to minute forces.

Figure 5B:
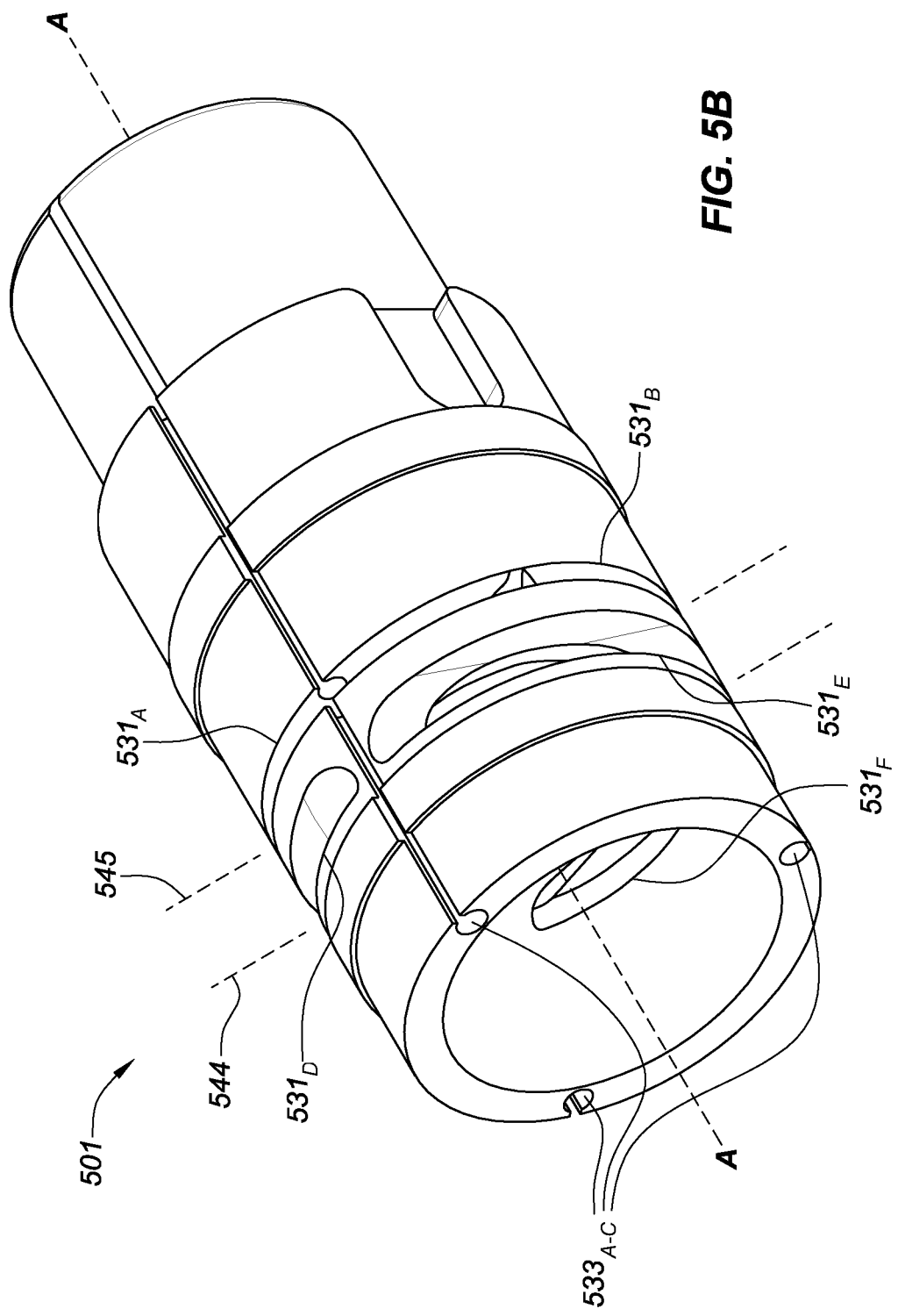
FIG. 5B is an isometric side view of a deformable body, consistent with various embodiments of the present disclosure.

FIG. 5B is an isometric side view of a deformable body 501 with six flexure portions $531_{A\text{-}F}$. Proximal flexure portions $531_{A\text{-}C}$ are circumferentially distributed around longitudinal axis A-A at first plane 545. Each of the flexure portions $531_{A\text{-}C}$ are rotationally offset by 120 degrees about axis A-A. Distal flexure portions $531_{D\text{-}F}$ are circumferentially distributed around longitudinal axis A-A at second plane 544. Each of the flexure portions $531_{D\text{-}F}$ are rotationally offset by 120 degrees. The proximal and distal flexure portions are further rotationally offset relative to one another by 120 degrees. This configuration facilitates placement of grooves $533_{A\text{-}C}$ directly through a mid-point of a proximal/distal flexure portion and between adjacent flexure portions of the distal/proximal flexure portions. As shown in FIG. 5B, the grooves $533_{A\text{-}C}$ are rotationally offset by 120 degrees. Accordingly, the grooves $533_{A\text{-}C}$ extend across midpoints of the proximal flexure portions and between distal flexure portions. In such an embodiment, the deflection of the proximal flexure portions are measured while the deflection of distal flexure portions are unmeasured, but absorb some of the force exerted on the deformable body 501. As discussed in more detail in reference to FIG. 6 below, the placement of the grooves $533_{A\text{-}C}$ with angular offsets of approximately 120 degrees improve phase-offset balance between each of the fiber optics placed therein.

In the embodiment depicted in FIG. 5B, the unmeasured distal flexure portions facilitate desired displacements at the proximal flexure portions, which are measured. Absent the three distal flexure portions, the deformable body 500 would be stiff under axial loading which may negatively impede force sensing accuracy of the system. It yet other embodiments, consistent with the present disclosure, the three proximal flexure portions may be unmeasured and the three distal flexure portions may be measured.

It is to be understood that the material characteristics and the dimensions of the deformable bodies disclosed herein may be calibrated to optimize the movement of the force sensing system in response to an expected range of forces exerted on a flexible tip for a given medical application or measurement system. While various embodiments of the present disclosure are directed to an optical measurement system, the deformable body may be calibrated to suit the specifications of a magnetic sensor-based deformation measurement system. For example, where the magnetic sensor has a resolution for detecting movement of a magnet of 0.1 millimeters, the material characteristics and dimensional characteristics for the deformable body may be selected for a given range of application forces (e.g., forces exerted on the flexible tip between 0-10 grams) that allows total use of the sensor resolution range. Similarly, the length of the deformable body may be selected in accordance with the off-axis sensor resolution and the angular off-axis displacement of the deformable body in response to a given range of trans-axial forces applied on the flexible tip.

The determined deflection of a deformable body may be compared with a calibration matrix to calculate a force exerted on a catheter tip. Material and shape selection (e.g., inner diameter, outer diameter, flexure portion dimensions, etc.) of the deformable body facilitates desired deformation characteristics.

Figure 6:
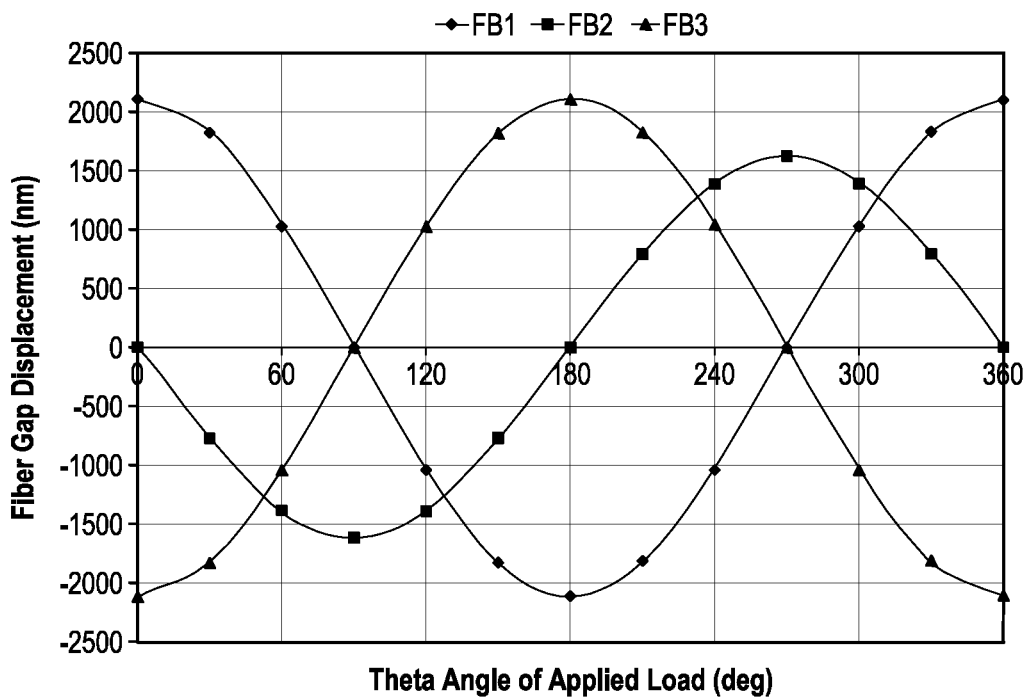
FIG. 6 is a graph charting theta angle of an applied load vs. fiber gap displacement as simulated for the deformable body of FIG. 5A, consistent with various embodiments of the present disclosure.

FIG. 6 is a graph charting theta angle of an applied load vs. fiber gap displacement as simulated for the deformable body of FIG. 5A, consistent with various embodiments of the present disclosure. As shown in FIG. 6, fiber optics 1-3 ("FB1," "FB2," and "FB3," respectively) are phase-offset by approximately 90 degrees. Accordingly, the four flexure portion design of deformable body 500 shows improved phase-offset balance to previous deformable body designs.

Figure 7:
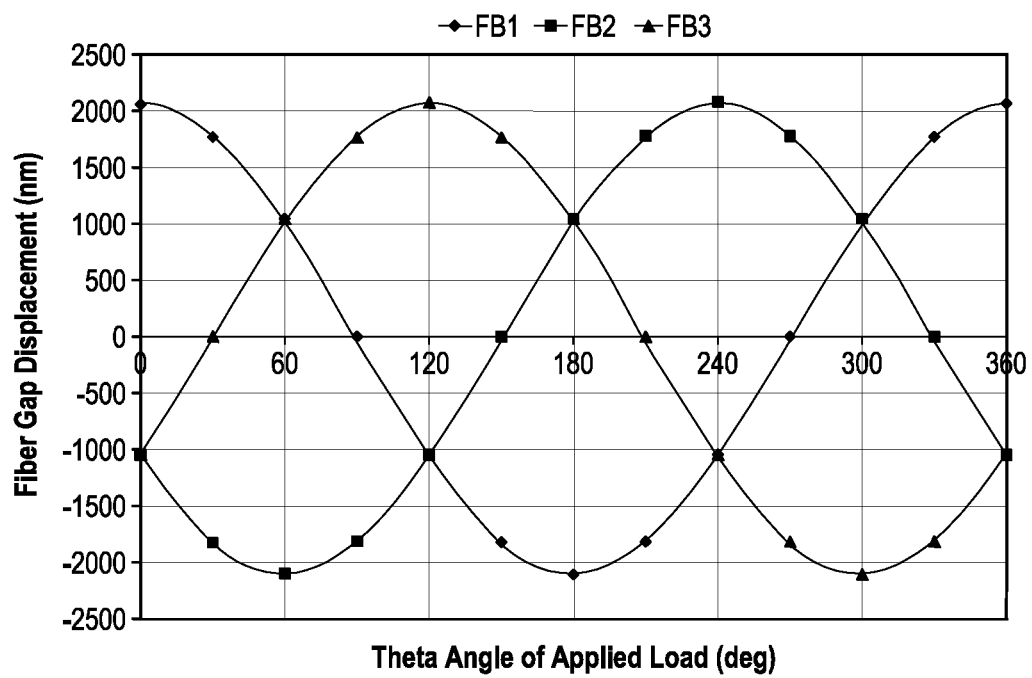
FIG. 7 is a graph charting theta angle of an applied load vs. fiber gap displacement as simulated for the deformable body of FIG. 5B, consistent with various embodiments of the present disclosure.

FIG. 7 is a graph charting theta angle of an applied load vs. fiber gap displacement as simulated for the deformable body of FIG. 5B, consistent with various embodiments of the present disclosure. As shown in FIG. 7, the four flexure portion design of deformable body 501, in combination with 120 degree angular offset of grooves $533_{A\text{-}C}$, shows improved phase-offset balance between each of the fiber optics—approximately 120 degrees between each of the fiber optics.

The finite element analysis simulation charted in FIGS. 6-7 is a 50 gram force laterally loaded in 30 degree increments circumferentially around the catheter tip.

Figure 8B:
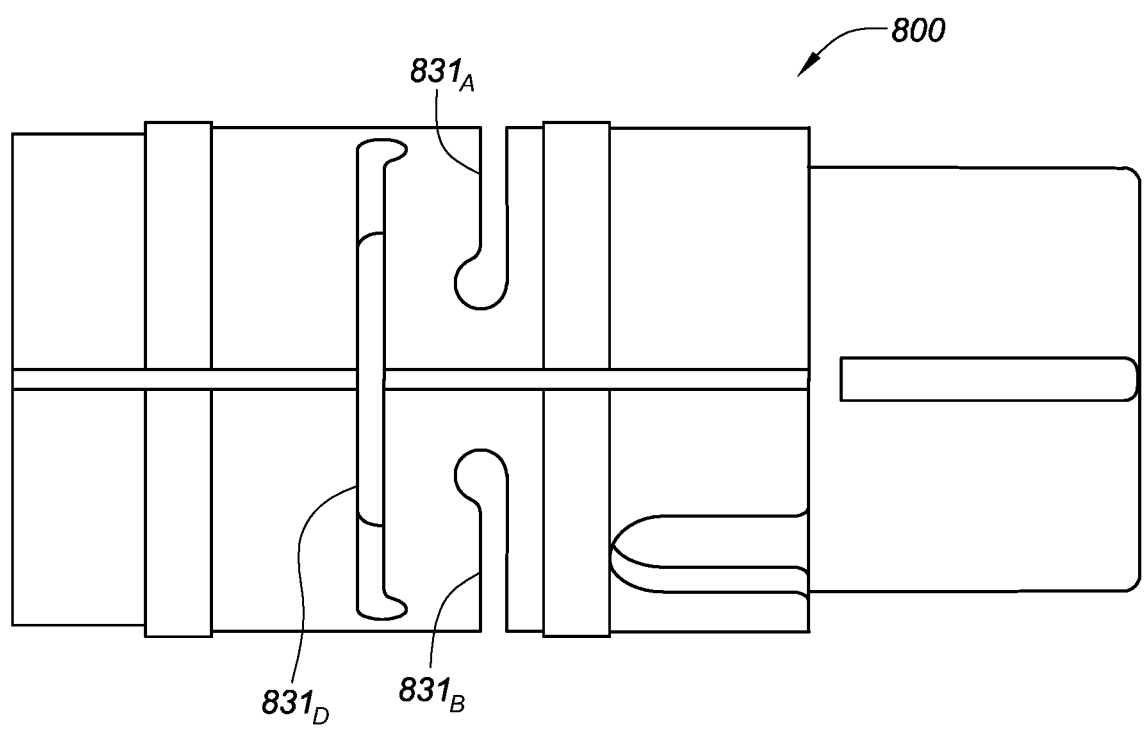
FIG. 8B is a front view of the deformable body of FIG. 8A, consistent with various embodiments of the present disclosure.
Figure 8C:
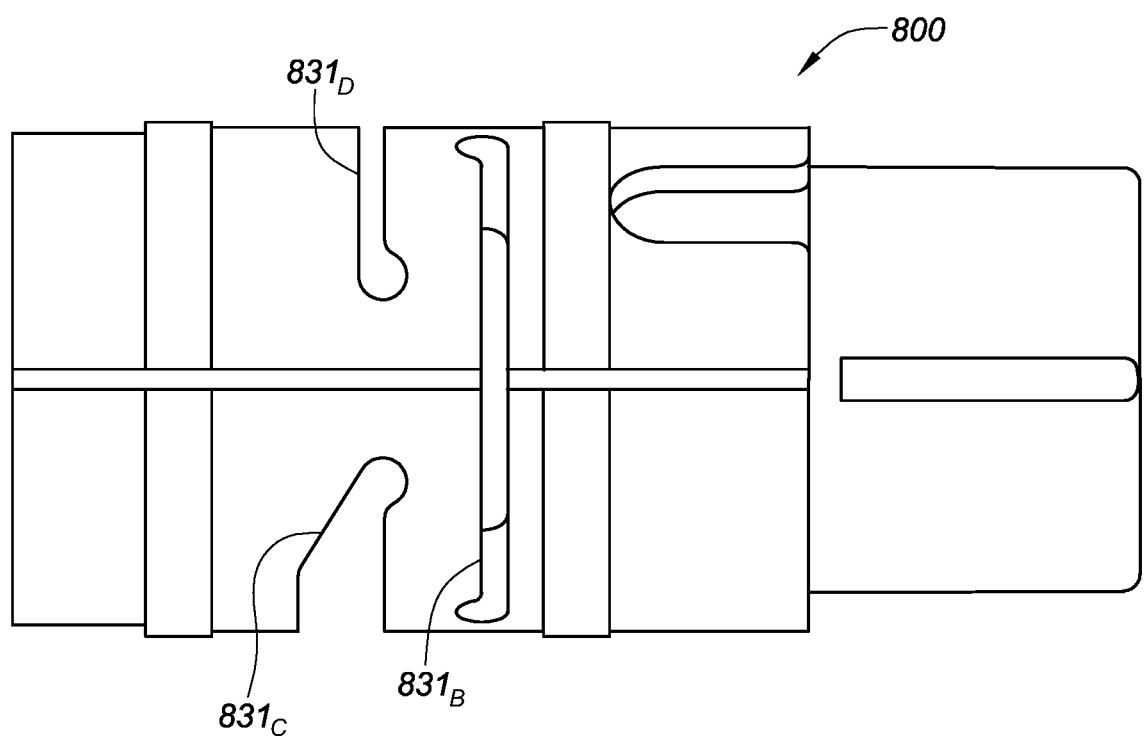
FIG. 8C is a side view of the deformable body of FIG. 8A, consistent with various embodiments of the present disclosure.

FIG. 8A is an isometric side view of a deformable body 800, FIG. 8B is a front view of the deformable body of FIG. 8A, and FIG. 8C is a side view of the deformable body of FIG. 8A, consistent with various embodiments of the present disclosure. As shown in FIGS. 8A-C, the deformable body 800 includes four flexure portions $831_{A\text{-}D}$. Two flexure portions $831_{A\text{-}B}$ circumferentially distributed about a proximal plane 845 and two flexure portions $831_{C\text{-}D}$ circumferentially distributed about a distal plane 844. Each of the flexure portions $831_{A\text{-}D}$ include a pair of strain reliefs 860. The strain reliefs of flexure portions $831_{A\text{-}B}$ extend distally, while the strain reliefs of flexure portions $831_{C\text{-}D}$ extend proximally. Further, the deflection of the flexure portion $831_C$ is not measured by an optical fiber. Flexure portion $831_C$ may be extended, for example, in a longitudinal direction (see, e.g., FIG. 8C) to facilitate assembly of a catheter including the deformable body 800. More specifically, the deformable body may partially house an irrigation lumen and/or thermocouple lead wires. Accordingly, during assembly, it may be advantageous to have an access window (e.g., flexure portion $831_C$) extending through the deformable body 800. In some embodiments, one or more flexure portions may have extended dimensions to facilitate ease of assembly or test.

Figure 9A:
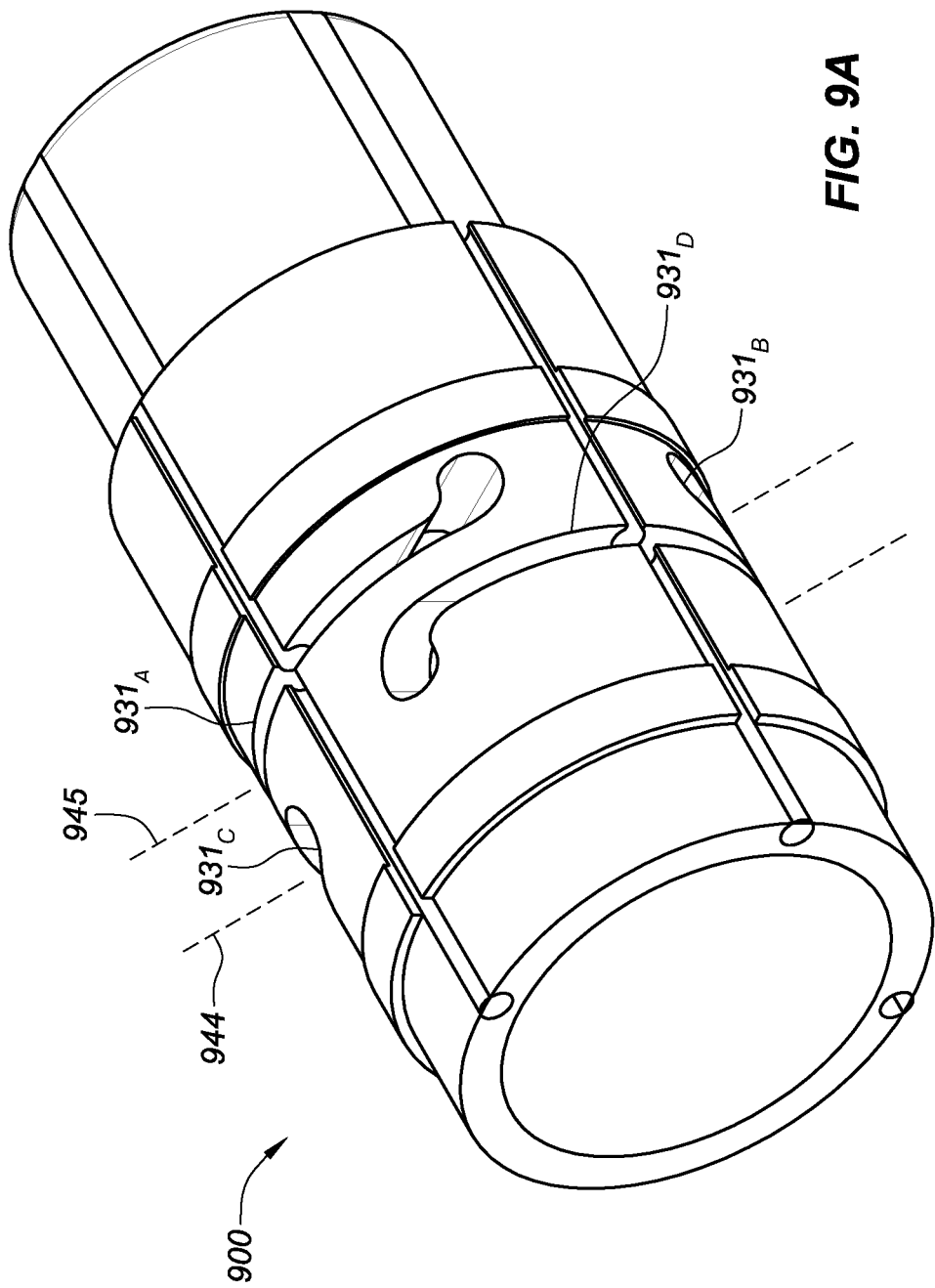
FIG. 9A is an isometric side view of a deformable body, consistent with various embodiments of the present disclosure.
Figure 9B:
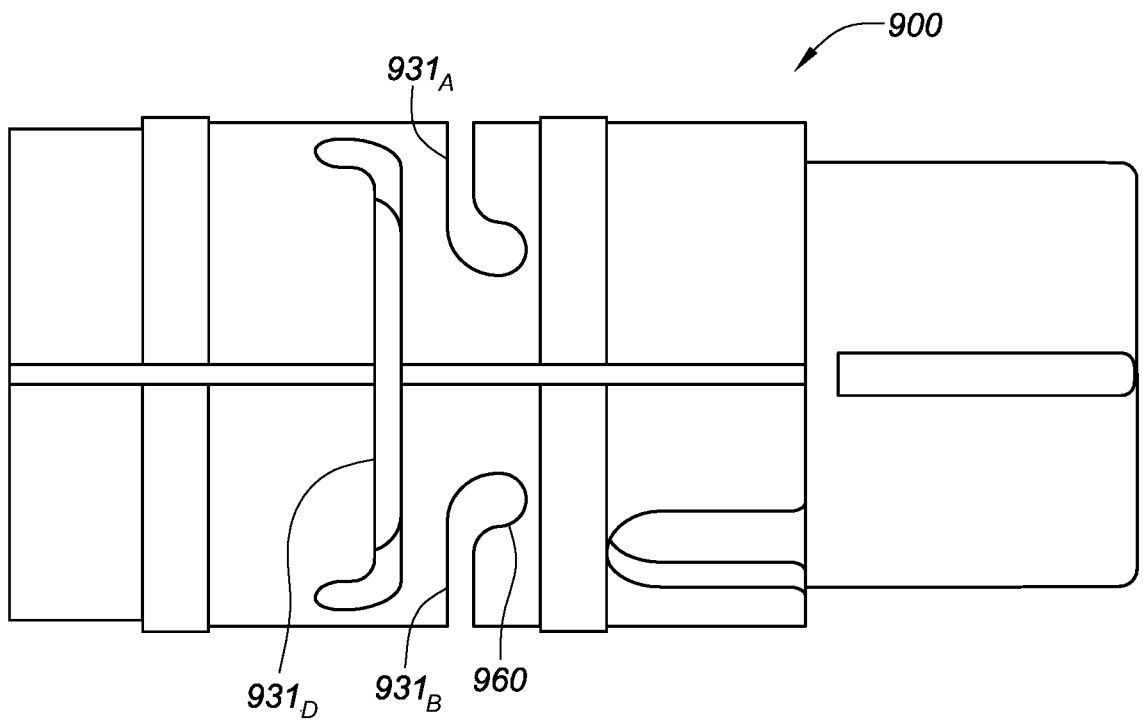
FIG. 9B is a front view of the deformable body of FIG. 9A, consistent with various embodiments of the present disclosure.
Figure 9C:
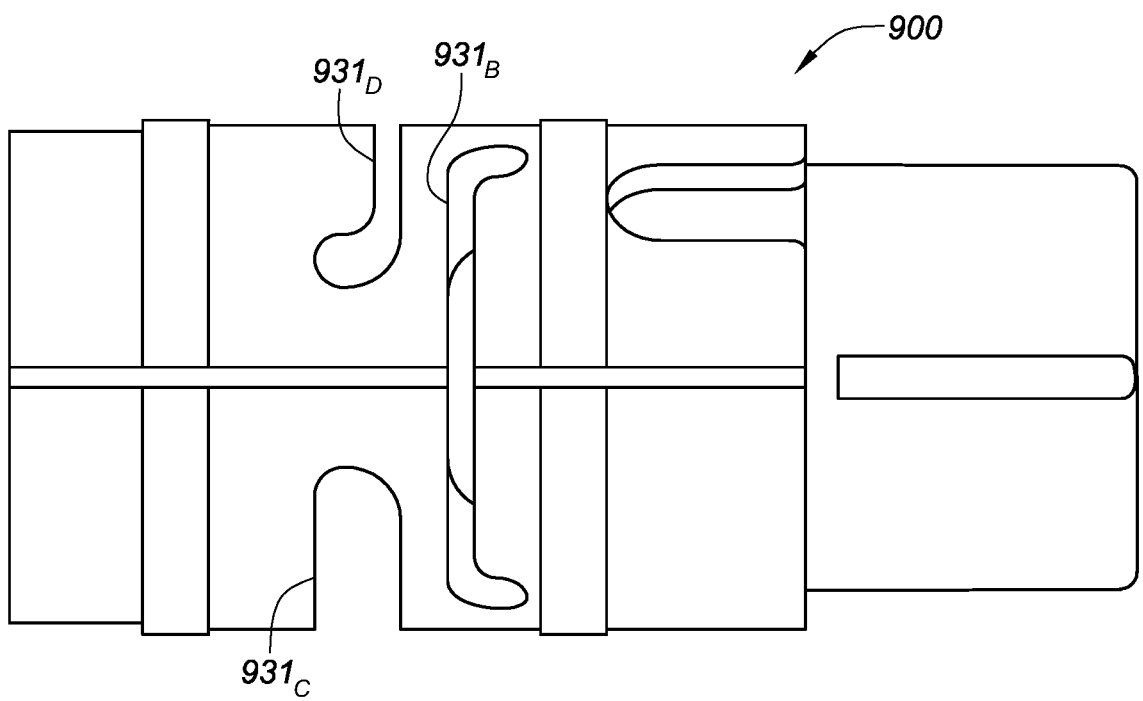
FIG. 9C is a side view of the deformable body of FIG. 9A, consistent with various embodiments of the present disclosure.

FIG. 9A is an isometric side view of a deformable body 900, FIG. 9B is a front view of the deformable body of FIG. 9A, and FIG. 9C is a side view of the deformable body of FIG. 9A, consistent with various embodiments of the present disclosure. As shown in FIGS. 9A-C, the deformable body 900 includes four flexure portions $931_{A-D}$. Two flexure portions $931_{A-B}$ are circumferentially distributed about a proximal plane 945 and two flexure portions $931_{C-D}$ are circumferentially distributed about a distal plane 944. Each of the flexure portions $931_{A-D}$ include a pair of strain reliefs 960. The strain reliefs of flexure portions $931_{A-B}$ extend proximally, while the strain reliefs of flexure portions $931_{C-D}$ extend distally. Applicant has discovered that the deformable body exhibits desirable deflection characteristics, for some applications, when the strain reliefs 960 extend away from one another. Specifically, such an embodiment exhibits reduce maximum stress by distributing the stress at the flexure portions over a larger area, instead of concentrated at a focal point (e.g., a corner).

Similar to FIGS. 8A-C, one or more of the flexure portion $931_{A-D}$ may facilitate assembly of a catheter assembly including the deformable body 900 by facilitating access to components within the deformable body (see, e.g., FIG. 9C—$931_C$).

While deformable bodies, in accordance with the present disclosure, have been discussed herein with four and six flexure portion configurations, various other implementations are readily envisioned; for example, 9 or more flexure portions.

While various embodiments of the present disclosure are discussed in reference to an ablation catheter, it is to be understood that a catheter consistent with the present disclosure may implement various different types of end effectors—e.g., mapping electrodes or ablation electrodes, such as are known in the art for diagnosis or treatment of a vessel or organ may be utilized with the present invention. For example, the catheter tip assembly may be configured as an electrophysiology catheter for performing cardiac mapping. In other embodiments, the catheter tip assembly may be configured to deliver drugs or bioactive agents to a vessel or organ wall, to perform minimally invasive procedures, and/or deliver an implantable medical device.

U.S. provisional application No. 62/331,292, filed 3 May 2016, U.S. application Ser. No. 15/585,859, filed 3 May 2017, international application no. PCT/US17/30828, filed 3 May 2017, U.S. provisional application No. 62/455,048, filed 6 Feb. 2017, U.S. provisional application No. 62/541, 805, filed 7 Aug. 2017, and U.S. provisional application No. 62/540,409, filed 2 Aug. 2017, are all hereby incorporated by reference as though fully set forth herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

When a single device or article is described herein, it will be readily apparent that more than one device or article can be used in place of a single device or article. Similarly, where more than one device or article is described herein, it will be readily apparent that a single device or article can be used in place of the more than one device or article. The functionality or the features of a device can be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various modules or other circuits can be implemented to carry out one or more of the operations and activities described herein and/or shown in the figures. In these contexts, a "module" is a circuit that carries out one or more of these or related operations/activities (e.g., processor circuitry). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A force-sensing catheter system comprising:
   a catheter tip; and
   a deformable body coupled to the catheter tip and configured and arranged to deform in response to a force exerted on the catheter tip, the deformable body including:
       an annulus with an inner surface and an outer surface,
       four flexure portions extending from the outer surface to the inner surface of the annulus, and
       three optical fiber grooves extending along the outer surface of the annulus, parallel to a longitudinal axis of the annulus, and each of the optical fiber grooves extending across at least one of the four flexure portions,
   wherein each of the four flexure portions includes strain reliefs provided at least at one end thereof, the strain reliefs configured and arranged to reduce the maximum stress experienced by the deformable body in response to the force exerted on the catheter tip.

2. The force-sensing catheter system of claim 1, wherein the optical fiber grooves are configured and arranged to position optical fibers across the flexure portions to measure the deflection of the annulus in response to a force exerted thereon.

3. The force-sensing catheter system of claim 1, wherein the flexure portions are circumferentially and longitudinally offset relative to one another.

4. The force-sensing catheter system of claim 1, wherein only a single optical fiber groove extends across a respective flexure portion.

5. The force-sensing catheter system of claim 1, wherein each optical fiber groove extends across a single flexure portion.

6. The force-sensing catheter system of claim 1, wherein each of the optical fiber grooves are circumferentially distributed about the longitudinal axis by approximately 120 degrees.

7. The force-sensing catheter system of claim 2, wherein, in response to the force exerted on the deformable body, the deformable body is configured and arranged to deflect and the resulting deflection measurements, sensed by each of the optical fibers in the optical fiber grooves have a phase shift between 90 degrees and 120 degrees relative to one another.

8. The force-sensing catheter system of claim 1, wherein first and second flexure portions are longitudinally offset relative to third and fourth flexure portions.

9. The force-sensing catheter system of claim 8, wherein the first and third flexure portions are circumferentially offset, relative to the second and fourth flexure portions, along the longitudinal axis of the annulus.

10. The force-sensing catheter system of claim 1, wherein the flexure portions extend approximately 180 degrees circumferentially around the annulus.

11. The force-sensing catheter system of claim 1, wherein one or more of the flexure portions extend approximately 120 degrees circumferentially around the annulus.

12. The force-sensing catheter system of claim 1, wherein the flexure portions include a proximal pair and a distal pair of flexure portions, wherein the strain reliefs of the proximal pair of flexure portions extend distally and the strain reliefs of the distal pair of flexure portions extend proximally.

13. The force-sensing catheter system of claim 1, further including:
    a measurement system coupled to the deformable body, the measurement system including three sensing elements coupled in proximity to at least one of the flexure portions and optical fiber grooves, the sensing elements configured and arranged to detect the deformation of the deformable body across the flexure portions, in response to the force exerted on the catheter tip, and transmit a signal indicative of the deformation; and
    processor circuitry communicatively coupled to the measurement system, and configured and arranged to receive the signal from each of the sensing elements, indicative of the deformation, and to determine a magnitude of the force exerted on the catheter.

14. The force-sensing catheter system of claim 13, wherein the sensing elements are optical fibers, and the signal indicative of the deformation are one or more photons.

15. The force-sensing catheter system of claim 13, wherein the processing circuitry is further configured and arranged to determine a time-of-flight of one or more photons across one of the flexure portions of the deformable body, and associate the time-of-flight of the photons with the force exerted on the catheter tip.

16. The force-sensing catheter system of claim 13, wherein the sensing elements are circumferentially distributed about the longitudinal axis by approximately 120 degrees.

17. The force-sensing catheter system of claim 13, further including a display communicatively coupled to the processor circuitry, wherein the processor circuitry is further configured and arranged to transmit data to the display indicative of the force exerted on the catheter tip, and the display is configured and arranged to visually communicate the force to a clinician.

18. The force-sensing catheter system of claim 13, wherein the resulting deflection measurements from each of the sensing elements, during a deflection of the deformable body, have a phase shift between 90 degrees and 120 degrees relative to one another.

19. The force-sensing catheter system of claim 13, wherein first and second flexure portions are longitudinally offset relative to third and fourth flexure portions along the deformable body.

20. The force-sensing catheter system of claim 19, wherein the first and third flexure portions are circumferentially offset, relative to the second and fourth flexure portions, along the longitudinal axis of the deformable body.

* * * * *